United States Patent [19]

Tober

[11] Patent Number: 5,064,283

[45] Date of Patent: Nov. 12, 1991

[54] SPECTROSCOPY CHARACTERIZATION MODULE

[75] Inventor: Richard L. Tober, Laurel, Md.

[73] Assignee: The United States of America as represented by the Secretary of the Army, Washington, D.C.

[21] Appl. No.: 407,186

[22] Filed: Sep. 14, 1989

[51] Int. Cl.$^5$ .......................... G01N 21/01; G01J 3/42
[52] U.S. Cl. ...................................... 356/73; 356/319; 356/323
[58] Field of Search .................. 356/73, 309, 319, 323, 356/326; 250/239

[56] References Cited

U.S. PATENT DOCUMENTS

| | | | |
|---|---|---|---|
| 3,958,882 | 5/1976 | Gast | 356/73 |
| 4,305,660 | 12/1981 | Kallet | 356/73 |
| 4,750,822 | 6/1988 | Rosencwaig et al. | 356/445 |
| 4,786,169 | 10/1988 | Brierley et al. | 356/244 |

OTHER PUBLICATIONS

Tober et al., "Piezoreflectance as a Supplement to Photoreflectance for Nondestructive Characterization of GaAs/AlxGa$_{1-x}$As Multiple Quantum Wells," J. Appl. Phys., vol. 64, No. 9, Nov. 1, 1988, pp. 4678–4682.
Tober et al., "Piezoreflectance Characterization of Double-Barrier Resonant Tunneling Structures," Appl. Phys. Lett., vol. 53, No. 10, Sep. 5, 1988, pp. 883–885.
Tober et al., "Piezoreflectance Characterization of Resonant Tunneling and Modulation-Doped Heterostructures," Journal of Electronic Materials, vol. 18, No. 3, 1989, pp. 379–384.
Tober et al., "Isomerization-Induced Evolution of Piezoreflectance Structures in Polyacetylene Films," Phys. Rev. B, vol. 33, No. 12, Jun. 15, 1986, pp. 8768–8771.
Handbook on Semiconductors, (T. S. Moss series ed., 1980) vol. 2, "Optical Properties of Solids," (M. Balkanski ed.) North-Holland Publishing Company, 110–154.

Primary Examiner—Vincent P. McGraw
Assistant Examiner—LaCharles P. Keesee
Attorney, Agent, or Firm—Saul Elbaum; Guy M. Miller

[57] ABSTRACT

A spectroscopy characterization module having a particular configuration includes a light tight housing that accepts monochromatic radiation through a first optical port and optically chopped coherent radiation through a second optical port. A material sample is held on a sample mount within the housing according to the spectroscopy characterization technique to be used. A rotatable detector mount enclosed within the housing positions a detector in different positions depending on the measurement being performed. A first one-to-one image forming mirror focuses monochromatic radiation passing through the first optical port onto the material sample. A lens focuses optically chopped radiation passing through the second optical port onto the material sample. A second one-to-one image forming mirror focuses radiation transmitted through the sample onto the detector in a first position while a third one-to-one image forming mirror focuses radiation reflected off the sample onto the detector in a second position. Various spectroscopic measurements can be performed on the material sample by merely using different sample mounts without changing the configuration of the characterization module.

15 Claims, 2 Drawing Sheets

SPECTROSCOPY CHARACTERIZATION MODULE

RIGHTS OF THE GOVERNMENT

The invention described herein may be manufactured, used and licensed by or for the United States Government for Governmental purposes without payment to me of any royalty thereon.

BACKGROUND THE INVENTION

1. Field of the Invention

The present invention relates to modulated and unmodualted material characterization techinques for characterizing materials and, more particularly, is directed towards a characterization module that has a unique configuration so that a variety of spectroscopy characterization techniques can be conveniently applied to material samples in a single apparatus. Using suitable material mounting adaptors, solids, liquids or even gases may be characterized.

2. Description of the Prior Art

Because of the recent advances in materials growth, for example with semiconductor materials and organic polymers, there is an ever increasing demand to utilize optical characterization techniques. These techniques include, but are not limited to photoreflectance, photomodulation, photoluminescence, thermoreflectance, thermomodulation, electroreflectance, electromodulation, piezoreflectance and piezmodulation. The position of optical transitions, as determined with the methods outlined above, provide information about alloy concentrations, doping or impurity concentrations, and epitaxial growth parameters.

The material characterization techniques mentioned above have been used for many years to determine material parametrs as described in the reference *Handbook on Semiconductors*, (T. S. Moss series ed., 1980) Vol. 2, "Optical Properties of Solids," North-Holland Publishing Company, 110-154, and references cited therein. For example, electroreflectance and photoreflectance spectroscopy has been used to evaluate surface states. In these techniques, the surface of a semiconductor is periodically excited either with an alternating electric field (electroreflectance) or an intensity modulated beam of light (photoreflectance). Changes in reflectivity in the sample due to this periodic excitation are then monitored. See U.S. Pat. No. 4,750,822 by Rosencwaig et al. which describes a method and apparatus for optically detecting surface states in materials.

However, it has become clear that more than one technique is often required to adequaely characterized the novel materials produced either by polymerization or epitaxial growth techniques. It has been shown that photoreflectance (a popular characterization method) could not be used to characterize an epitaxially grown quantum well sample but it could easily be characterized using piezoreflectance techniques in an article entitled, "Piezoreflectance as a Supplement to Photoreflectance for Nondestructive Characterization of GaAs-/$Al_xGa_{1-x}As$ Multiple Quantum Wells," Tober et al., J. Appl. Phys., Vol. 64, No. 9, 1 Nov. 1988, pp. 4678-4682. Because of growth parameters piezoreflectance can be used to characterized double-barrier resonant tunneling devices but other optical techniques cannot. On the other hand, a class of epitaxially grown structures exists that, for one reason or another, can only be adequately characterized using a combination of complimentary modulation techniques as described in an article entitled "Piezoreflectance Characterization of Resonant Tunneling and Modulation-Doped Heterostructures", Tober et al., Journal of Electronic Materials, Vol. 18, No. 3, 1989, pp. 379-384. Polymers can also be characterized using modulated optical techniques as described in "Isomerization - Induced Evolution of Pieozreflectance Structures in Polyacetylene Films," Tober et al., Phys. Rev. B. Vol. 33, No. 12, 15 Jun. 1986, pp. 8768-8771.

Currently, there is no convenient single apparatus to test a particular material that can incorporate all the various modulation spectroscopy techniques. Each apparatus requires its own specific geometrical configuration and components (optical and electronic). Consequently, it is desirable to be able to have an apparatus that provides a simple means for performing these material characterization techniques in a single apparatus or module.

SUMMARY OF THE INVENTION

It is therefore a primary object of the invention to provide a materials characterization module that can be used to evaluate a material sample using a variety of spectroscopic techniques without having to change the module configuration.

It is a further object of the invention to provide a material characterization module that permits a material sample to be mounted in such a way as to permit its optical properties to be modulated with a variety of complimentary methods.

The foregoing and other objects are attained in accordance with the invention through the use of a light tight housing having first and second optical ports that permit the transmission of monochromatic and/or coherent radiation therethrough. While any material such as solids, liquids and gases can be analyzed using the spectroscopy characterization module by using suitable material mounts, the following description will be directed primarily to, but not limited by, solid materials for ease of explanation. A solid material sample mount is positoned within the housing with a solid material sample mounted according to the technique to be used. A rotatable detector mount within the housing positions a detector in either of one of two positions depending on the measurement being performed. A first toroidal or spherical mirror is positioned within the housing for focusing a substantially one-to-one image of the monochromatic radiation transmitted through the first optical port onto the solid material sample. A lens focuses optically chopped radiation transmitted through the second optical port onto the solid material for modulating the optical properties of the sample probed by the monochromatic radiation. A second toroidal or spherical mirror positioned within the housing focuses a substantially one-to-one image of the monochromatic radiation transmitted through the solid material sample onto the detector in a first position while a third toroidal or spherical mirror positioned within the housing focuses a substantially one-to-one image of the monochromatic radiation reflected off the solid material sample onto the detector in a second position. The prefered placement of the mirrors in such that one-to-one images of radiation transmitted or reflected from the solid material sample are focused onto the detector. Rotating the detector mount allows measurements to be taken of transmitted radiation in a first position and of reflected radiation in a second position.

The foregoing and other objects and advantages of the invention will appear from the following description. In the description reference is made to the accompanying drawings which form a part hereof, and in which there is shown by way of illustration and not of limitation a preferred embodiment. Such description does not represent the full extent of the invention, but rather the invention may be employed in different arrangements according to the breadth of the invention.

DESCRIPTION OF THE PREFERRED EMBODIMENTS

Figure 1:
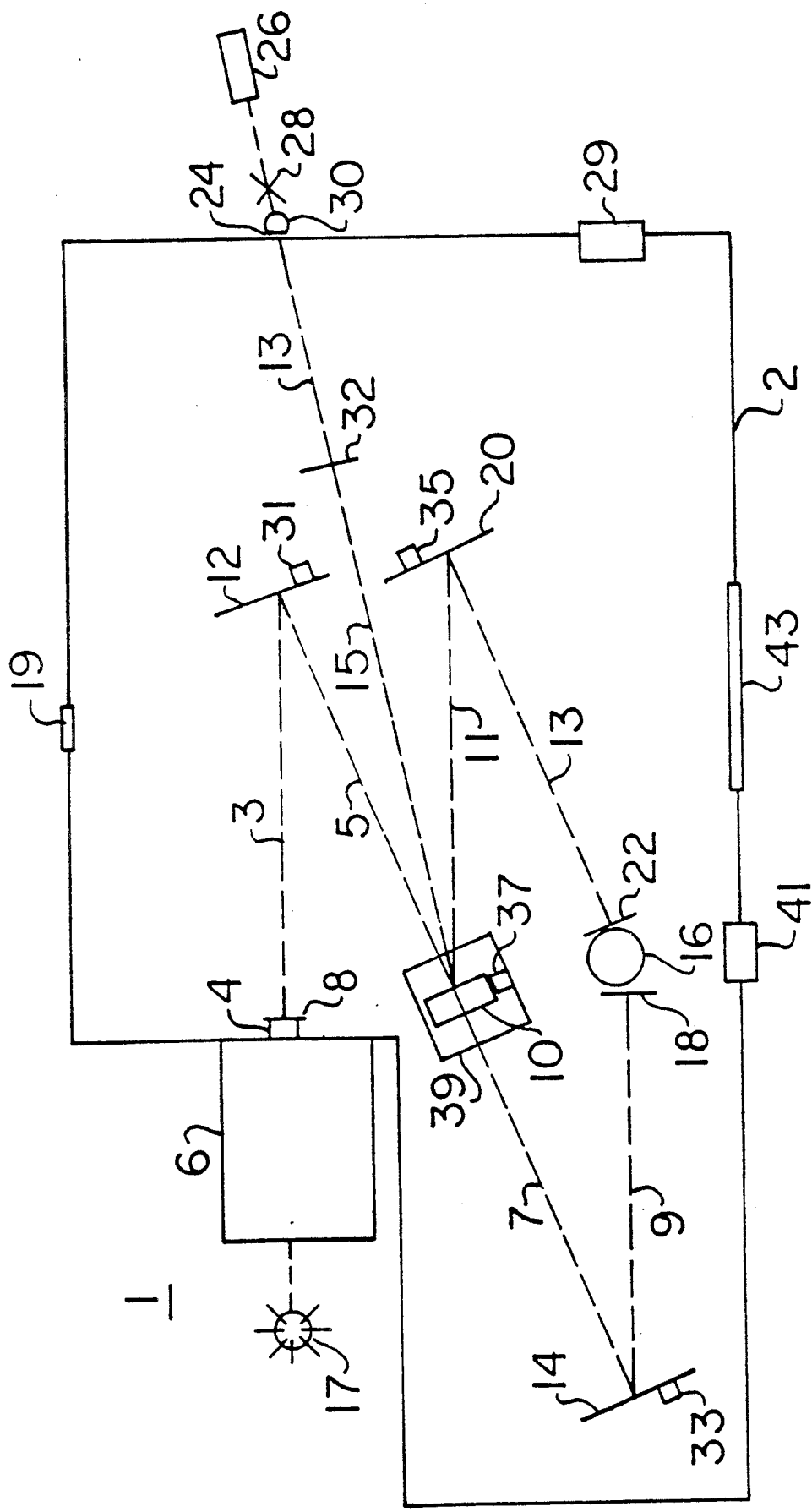
FIG. 1 shows in symbolic form a modulation spectroscopy characterization module according to an aspect of the invention.

Referring now to the drawings, like reference numerals represent identical or corresponding parts throughout the several views.

The preferred embodiment of the invention is shown in FIG. 1. A materials characterization module 1 is shown comprising a light tight housing 2 having an optical port 4 in which broadband radiation from a broadband radiation source 17 dispersed through a monochromator 6 and filter 8 is passed therethrough. The light tight housing 2 can be a vacuum aluminum housing allowing for the purging of gases through orifice 19. The filter can be used to eliminate n>1 diffraction orders. While the filter 8 is shown enclosed within the light tight housing 2 it could easily be placed outside the housing 2 as is the monochromator 6. The monochromatic radiation from the monochromator 6 propagates along path 3 and is focused onto a material sample mounted on a sample mount 10 using either a toroidal or spherical mirror 12. The mirror 12 ia positioned within the housing 2 so that the monochromatic radiation reflects off the mirror 12 and propagates along path 5 to produce a one-to-one image of the optical port 4 on the sample. The optical port 4 is capable of being reduced to, for example, from a 2000 micrometer by 2000 micrometer square or 2000 micrometer diameter circle to a 100 micrometer by 100 micrometer square or a 100 micrometer diameter circle or smaller.

Monochromatic radiation transmitted through the sample propagates along path 7 to either to a toroidal or spherical mirror 14 which focuses a substantially one-to-one image onto a detector held in place by a rotatable detector mount 16 through a filter held by filter holder 18 along path 9. Monochromatic radiation reflected off the sample propagates along path 11 to either a toroidal or spherical mirror 20 which focuses a one-to-one image onto the detector held by the detector mount 16 through a filter held by filter holder 22 along path 13. The detector mount 16 is designed to rotate a detector from a first position in which the detector detects radiation focused from mirror 14 to a second position in which the detector detects radiation focused from mirror 20. For example, the detector mount could merely be attached to a cylindrical peg which rotatably fits in a circular slot allowing an operator to rotate the detector to the desired position. The detector mount 16 is also designed to accept multiple detectors to cover a wide spectral range. The filter holders 18 and 22 located adjacent the detector mount 16 accept filters selected to eliminate unwanted radiation signals.

To perform additional tests the light tight housing 2 can also include an optical port 24 in which coherent radiation from a laser (or additional monochromator) 26 which has been optically chopped by an optical chopper 28 and filtered by a band pass filter or optical fiber 30 is transmitted therethrough. The coherent radiation from the laser 26 propagates along path 13 through a lens 32 which focuses the coherent radiation along path 15 onto the sample mounted on sample mount 10. The band pass filter 30 (or optional optical fiber) allows only the laser radiation to be transmitted into the light tight chamber 2.

The unique configuration of the materials characterization module 1 with toroidal or spherical mirrors 12, 14 and 20 frequency matched to the monochromator 6 and preferably positioned to focus substantially one-to-one images onto a sample mounted on sample mount 10 allows for the testing of the sample using various characterization techniques without the need for having a different test apparatus for each test. For ease of focusing, the mirrors 12, 14 and 20 can be mounted on X-Y-Z translators, represented by blocks 31, 33 and 35 respectively, which can accurately shift the mirrors to their proper focal position within the module. Modifying the way in which the sample is mounted on the sample mount 10 determines the type of characterization measurements that can be made. For ease of testing a particular material the sample mount 10 can be also be mounted on an X-Y-Z translator represented by block 37. The sample mount 10 can also be refrigerated by enclosing it in a refrigerator 39. The light tight housing 2 cna also be purged with gases through orifice 19 that have minimum absorptions in the spectral region of interest. For example, Nitrogen gas could be used for the near ultra violet spectral region. A simple door or shield 43 covering an opening in the housing 1 can be used to allow easy placement and removal of samples within the housing 1.

Figure 3:
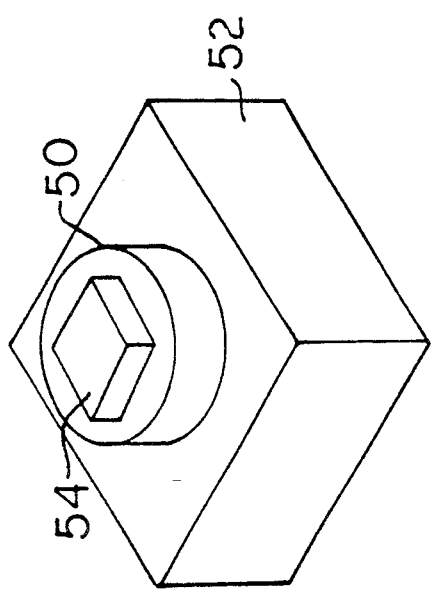
FIG. 3 shows an oblique pictorial view of a typical solid material sample mount for use in the modulation spectroscopy characterization module during piezoreflectance measurements.
Figure 2:
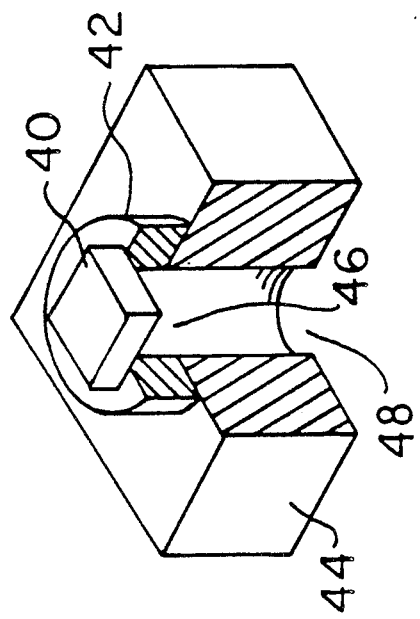
FIG. 2 shows an oblique pictorial view, partially in section, of a typical solid material sample mount for use in modulation spectroscopy characterization module during piezomodulation measurements.

Modulated optical measurements are performed by perturbing the optical properties of the sample at a desired frequency and monitoring the changes in reflectance or transmission measured at the detector. Any suitable detector can be used such as silicon PIN photodiodes or photomultiplier tubes that can cover a spectral range from at least, but not limited to 0.2 micrometers to 40 micrometers. The changes in the optical properties are measured using a lock-in amplifier tuned to the modulation frequency. For example, piezomodualtion is accomplished by rigidly attaching the sample to a piezoelectric transducer. A lead-zirconate-titanate piezoelectric transducer or piezotransducer in which the sample is glued to the piezotransducer can be used. A periodic voltage applied to the transducer modulates the optical properties of the sample. As shown in FIG. 2 piezoreflectance and piezotransmittance measurements can be accomplished by having a solid material sample 40 rigidly attached to a piezotransducer 42 which is rigidly attached to a metal mount 44. The piezotransducer 42 and metal mount 44 each have a passage 46 and 48 respectively extending therethrough to allow for both modulated reflectance and modulated transmission measurements. As previously indicated, the sample mount 44 can be enclosed within a refrigerator 39 equipped with optical windows for low temperature measurements. The refrigerator 39 and sample mount 44 are attached to an X-Y-Z translator 37 so that the entire sample surface can be characterized. Both the refrigerator 39 and X-Y-Z translator 37 are well known to those skilled in the art. In the case where a solid material sample is too small for transmission measurements FIG. 3 shows a solid material sample 54 glued to a piezotransducer 50 and metal mount 52 without any passage extending therethrough for performing piezoreflectance measurements.

Photomodulation of optical properties is accomplished by chopping a laser beam (or radiation from a second monochromator) from laser 26 incident on the sample. Referring back to FIG. 1 photoluminescence measurements are accomplished by having radiation from laser (or second monochromator) 26 transmit through optical port 24 and irradiate the sample after being focused by the lens 32. The optical chopper 28 modulates the intensity of radiation so that phase sensitive lock-in techniques can be used to measure the photoluminescence signals emanating from the sample.

Figure 4:
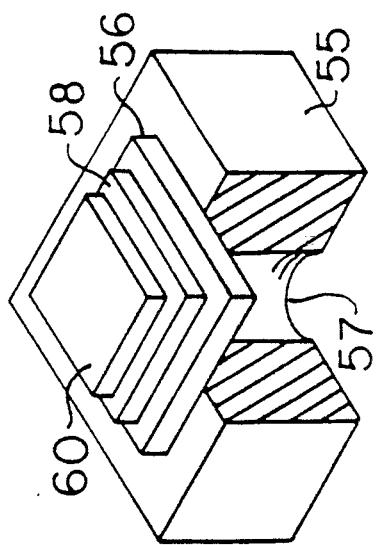
FIG. 4 shows an oblique pictorial view, partially in section, of a typical solid material sample mount for use in the modulation spectroscopy characterization module during longitudinal electromodulation measurements.
Figure 5:
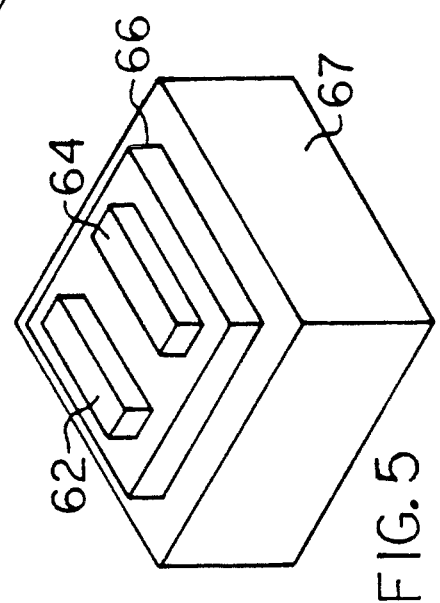
FIG. 5 shows an obliue pictorial view of a typical solid material sample mount for use in the modulation spectroscopy characterization module during transverse electromodulation measurements.

Electric field modulation is accomplished by affixing electrodes to the sample and applying a periodic potential to them. Two electrode configurations are possible. A first configuration is shown in FIG. 4 where an electrode 56 is positioned on one side of the sample 58 and a semitransparent electrode 60 is positioned on the other side of the sample 58. These electrodes create an electric field that is substantially parallel to the plane of incidence providing longitudinal electromodulation. If modulated transmission measurements are to be made the mount 55 must have a passage 57 therethrough and the electrode 56 must be semitransparent. A seocnd configuration is shown in FIG. 5 where a first electrode 62 is separated from a second electrode 64 by about 0.5 mm and each attached to material sample 66 which is mounted on mount 67. The electrodes 62 and 64 create an electric field that is substantially perpendicular to the plane of incidence providing transverse electromodulation.

Figure 6:
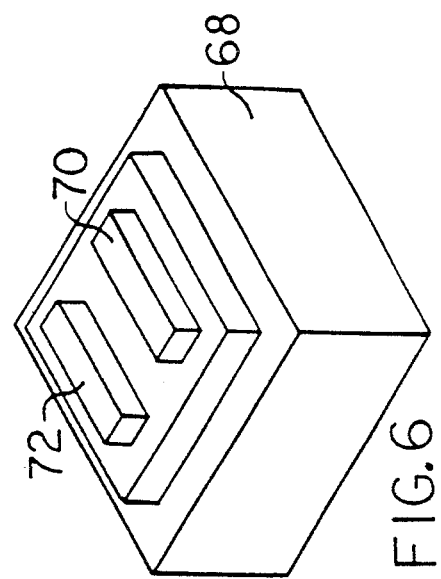
FIG. 6 shows an oblique pictorial view of a typical solid material sample mount for use in the modulation spectroscopy characterization module during thermomodulation measurements.

Thermomodulation requires at least one resistive heater to be affixed to the sample. FIG. 6 shows a configuration where a sample 68 has two resistive heaters 70 and 72. A periodic current passing through the heaters 70 and 72 heat the sample thereby modulating its optical properties.

The electrical power for thermomodulation, electric field modulation, and piezomodulation is fed through the light tight chamber 2 via bulk head feed through 29.

The same feed through 29 or another feed through 41 can be used for obtaining the signal at detector 16.

In every technique mentioned above the same characterization module can be used. Only changes in sample mounts are necessary to perform the various tests. External electronic equipment requirements can include a lock-in amplifier for phase sensitive detection, a signal generator and amplifier capable of supplying up to 1000volts peak-to-peak for piezomodulation and electric field modulation, a programmable voltage source that can supply several amps of current for thermomodulation, and a desk top computer with interfacing capabilities for data acquisition and for controlling the monochromator and any refrigerator or modulation electronics.

Obviously, numerous modifications and variations of the present invention are possible in light of the above teachings. It is therefore to be understood that within the scope of the appended claims, the invention may be practiced otherwise than as specifically described herein.

What is claimed is:

1. A spectroscopy characterization module having a particular configuration comprisng:
    a light tight housing for performing spectroscopy measurements having a firt optical port for passing monochromatic radiation therethrough;
    means for holding a material sample disposed within said light tight housing;
    first image focusing means for producing an image of the monochromatic radiation passing through the first optical port onto the material sample; p1 a detector mount disposed within said housing for holding a detector in a first position for detecting radiation transmitted through the material sample for holding the detector in a second position for detecting radiation reflected off the material sample;
    second image focusing means for producing an image of radiation transmitted through the material sample onto the detector in the first position; and
    third image focusing means for producing an image of radiation reflected off the material sample onto the detector in the second position;
    whereby various spectroscopic measurements can be performed on the material sample without changing the configuration of the characterization module.

2. The spectroscopy characterization module of claim 1 wherein each of said image focusing means produces a substantially one-to-one image of radiation focused thereby.

3. The spectroscopy characterization module of claim 1 wherein said light tight housing has a second optical port for passing optically chopped coherent radiation therethrough.

4. The spectroscopy characterization module of claim 3 wherein each of said image focusing means produces a substantially one-to-one image of radiation focused thereby.

5. The spectroscopy characterization module of claim 3 further comprising:
    forth image focusing means for focusing the optically chopped coherent radiation passing through the second optical port onto the material sample modulating the optical properties of the material sample.

6. The spectroscopy characterization module of claim 5 wherein said forth image focusing means comprises a lens.

7. The spectroscopy characterization module of claim 1 wherein the area of said first optical port is adjustable.

8. The spectroscopy characterization module of claim 1 wherein said light tight housing can be purged with gases.

9. The spectroscopy characterization module of claim 1 wherein each of said image focusing means comprises a toroidal mirror.

10. The spectroscopy characterization module of claim 1 wherein each of said image focusing means comprises a spherical mirror 11. The spectroscopy characterization module of claim 1 further comprising:
   first three dimensionally adjustable positioning means mounted to said first image focusing means for shifting said first image focusing means to a position that produced a substantially one-to-one image of the monochromatic radiation passing through the first optical port onto the material sample;
   second three dimensionally adjustable positioning means mounted to said second image focusing means for shifting said second image focusing means to a position that produces a substantially one-to-one image of radiation transmitted through the material sample onto the detector in the first position;
   third three dimensionally adjustable psotioning means mounted to said third image focusing means for shifting said third image focusing means to a position that produces a substantially one-to-one image of radiation reflected off the material sample onto the detector in the second position.

12. The spectroscopy characterization module of claim 11 further comprising:
   fourth three dimensionally adjustable positioning means mounted to said means for holding a material sample for shifting said means for holding the material sample to multiple positions.

13. The spectroscopy characterization module of claim 1 wherein said detector mount is rotatable.

14. A spectroscopy characterization module having a particular configuration comprising:
   a light tight housing for performing spectroscopy measurements having a first optical port for passing monochromatic radiation therethrough and a second optical port for passing optically chopped coherent radiation therethrough;
   means for holding a material sample disposed within said light tight housing;
   first image focusing means for focusing monochromatic radiation passing through the first optical port onto the material sample producing a substanially one-to-one image of the monochromatic radiation passing through the first optical port on the material sample;
   a rotatabe detector mount disposed within said housing for holding a detector in a first position that detects radiation transmitted through the material sample and for holding the detector in a second position that detects radiation reflected off the materials sample;
   second image focusing means for focusing radiation transmitted through the material sample onto the detector producing a substantially one-to-one image of the radiation transmitted through the material sample onto the detection the first position;
   third image focusing means for focusing monochromatic radiation reflected off the material sample onto the detector producing a substantially one-to-one image of the radiation reflected off the material sample onto the detector in the second position; and
   forth image focusing means for focusing the optically chopped coherent radiation passing through the second optical port onto the material sample so that the opticl properties of the material sample are modulated by the optically chopped coherent radiation;
   whereby various spectroscopic mesurements can be performed on the material sample without changing the configuration of the characterization module.

15. A spectroscopy characterization module having a particular configuration comprising:
   a light tight housing for performing spectroscopy measurements having a first optical port for passing monochromatic radiation therethrough and a second optical port for passing optically chopped coherent radiation therethrough;
   a material sample mount disposed within said housing for holding a material sample;
   a first filter holder disposed wihtin said housing for holding a first filter;
   a second filter holder disposed within said housing for holding a second filter;
   a first one-to-one image forming mirror for focusing monochromatic radiation passing through the first optical port onto the material sample;
   a rotatable detector mount disposed within said housing for holding a detector in a first position for detecting radiation transmitted through the sample and for holding the detector in a second position for detecting radiation reflected off the sample;
   a second one-to-one image forming mirror for focusing radiation transmitted through the material sample onto the detector in the first position through the first filter;
   a third one-to-one image forming mirror for focusing radiation reflected off the material shape onto the detector in the second position through the second filter; and
   a lens disposed within said housing for focusing the optically chopped coherent radiation passing through the second optical port onto the material sample so that the optical properties of the material sample are modulated by the optically chopped coherent radiation;
   whereby various spectroscopic measurements can be performed on the material sample without changing the configuration of the characterization module.

* * * * *